United States Patent
Li et al.

(10) Patent No.: US 6,831,094 B2
(45) Date of Patent: Dec. 14, 2004

(54) HETEROCYCLYLALKOXY-, -ALKYLTHIO-AND -ALKYLAMINOBENZAZOLE DERIVATIVES AS 5-HYDROXYTRYPTAMINE-6 LIGANDS

(75) Inventors: Yanfang Li, Lawrenceville, NJ (US); Ping Zhou, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/126,805

(22) Filed: Apr. 19, 2002

(65) Prior Publication Data

US 2003/0078286 A1 Apr. 24, 2003

Related U.S. Application Data

(60) Provisional application No. 60/285,644, filed on Apr. 20, 2001.

(51) Int. Cl.[7] .................. A61K 31/40; C07D 403/12
(52) U.S. Cl. .......................... 514/414; 548/465
(58) Field of Search .................. 514/414; 548/465

(56) References Cited

U.S. PATENT DOCUMENTS

| | | | |
|---|---|---|---|
| 5,037,841 A | | 8/1991 | Schohe et al. |
| 5,453,437 A | * | 9/1995 | Schohe et al. .............. 514/424 |
| 6,054,469 A | | 4/2000 | Bourrain |
| 6,509,357 B1 | * | 1/2003 | Zhou et al. .................. 514/322 |

FOREIGN PATENT DOCUMENTS

| | | | |
|---|---|---|---|
| JP | 09040646 A2 | | 2/1997 |
| JP | 09-040646 | * | 2/1997 |
| WO | WO 95/03298 A1 | | 2/1995 |
| WO | WO 01/05758 A2 | | 1/2001 |

OTHER PUBLICATIONS

Branchek et al. "5–HT6 receptors as emerging targets for drug discovery" CA 133:98965 (2000).*

Audia et al. "Preparation of3–(4–indolyloxy) . . . " CA 125:168021 (1996).*

* cited by examiner

*Primary Examiner*—Celia Chang
(74) *Attorney, Agent, or Firm*—Barbara L. Lences

(57) ABSTRACT

The present invention provides a compound of formula I and the use thereof for the therapeutic treatment of disorders relating to or affected by the 5-HT6 receptor.

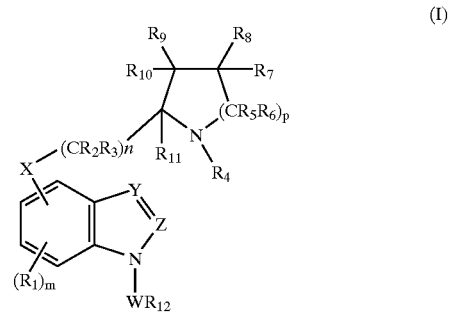

12 Claims, No Drawings

HETEROCYCLYLALKOXY-, -ALKYLTHIO-AND -ALKYLAMINOBENZAZOLE DERIVATIVES AS 5-HYDROXYTRYPTAMINE-6 LIGANDS

This application claims priority from copending application Ser. No. 60/285,644, filed on Apr. 20, 2001, the entire disclosure of which is hereby incorporated by reference.

BACKGROUND OF THE INVENTION

Various central nervous system disorders such as anxiety, depression, motor disorders, etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. The effects of serotonin are regulated by the various 5-HT receptor subtypes. Known 5-HT receptors include the 5-HT1 family (e.g. 5-HTIA), the 5-HT2 family (e.g. 5-HT2A), 5-HT3, 5-HT4, 5-HT5, 5-HT6 and 5-HT7 subtypes.

The recently identified human 5-hydroxytryptamine-6 (5-HT6) receptor subtype has been cloned, and the extensive distribution of its mRNA has been reported. Highest levels of 5-HT6 receptor mRNA have been observed in the olfactory tubercle, the striatum, nucleus accumbens, dentate gyrus and CA1, CA2 and CA3 regions of the hippocampus. Lower levels of 5-HT6 receptor mRNA were seen in the granular layer of the cerebellum, several diencephalic nuclei, amygdala and in the cortex. Northern blots have revealed that 5-HT6 receptor mRNA appears to be exclusively present in the brain, with little evidence for its presence in peripheral tissues. The high affinity of a number of antipsychotic agents for the 5-HT6 receptor, in addition to its mRNA localization in striatum, olfactory tubercle and nucleus accumbens suggests that some of the clinical actions of these compounds may be mediated through this receptor. Therefore, 5-HT6 receptor ligands are believed to be of potential use in the treatment of certain CNS disorders such as anxiety, depression, epilepsy, obsessive compulsive disorders, attention deficit disorder, migraine, cognitive memory enhancement (e.g. for the treatment of Alzheimer's disease), sleep disorders, feeding disorders (e.g. anorexia and bulimia), panic attacks, withdrawal from drug abuse (e.g. cocaine, ethanol, nicotine and benzodiazepines), schizophrenia, or the like; or in the treatment of certain gastrointestinal disorders such as irritable bowel syndrome.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides a compound of formula

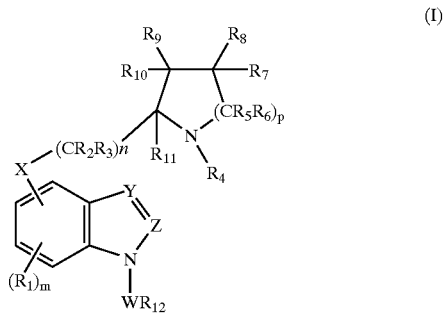

(I)

wherein
W is $SO_2$, CO, CONH, CSNH or $(CH_2)_x$;
X is O, $SO_y$ or $NR_{13}$;
Y is $CR_{14}$ or N;
Z is $CR_{15}$ or N with the proviso that when Y is N then Z must be $CR_{15}$;
m and x are each independently 0 or an integer of 1, 2 or 3;
n and p are each independently an integer of 1, 2 or 3;
$R_1$ is halogen, CN, $OR_{16}$, $CO_2R_{17}$, $CONR_{18}R_{19}$, $CNR_{20}NR_{21}R_{22}$, $SO_2NR_{23}R_{24}$, $SO_wR_{25}$, or a $C_1$–$C_6$alkyl, $C_2$–$C_6$alkenyl, $C_2$–$C_6$alkynyl, $C_3$–$C_6$cycloalkyl, cycloheteroalkyl, phenyl or heteroaryl group each optionally substituted;
$R_2$, $R_3$, $R_5$, $R_6$, $R_7$, $R_8$, $R_9$, $R_{10}$ and $R_{11}$ are each independently H or an optionally substituted $C_1$–$C_6$alkyl group;
$R_4$ is H, $CNR_{26}NR_{27}R_{28}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_{12}$ is an optionally substituted $C_1$–$C_6$alkyl, aryl or heteroaryl group;
y and w are each 0 or an integer of 1 or 2;
$R_{13}$ is H or a $C_1$–$C_6$alkyl, $C_2$–$C_6$ alkenyl, $C_2$–$C_6$alkynyl, $C_3$–$C_6$cycloalkyl, cycloheteroalkyl, aryl or heteroaryl group each optionally substituted;
$R_{14}$ and $R_{15}$ are each independently H, halogen or a $C_1$–$C_6$alkyl, aryl, heteroaryl or $C_1$–$C_6$alkoxy group each optionally substituted;
$R_{16}$ is H, $COR_{29}$ or a $C_1$–$C_6$alkyl, $C_2$–$C_6$alkenyl, $C_2$–$C_6$alkynyl, aryl or heteroaryl group each optionally substituted;
$R_{17}$ and $R_{29}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_{18}$, $R_{19}$, $R_{20}$, $R_{21}$ $R_{22}$, $R_{26}$, $R_{27}$, and $R_{28}$ are each independently H or an optionally substituted $C_1$–$C_6$alkyl group;
$R_{23}$ and $R_{24}$ are each independently H or a $C_1$–$C_6$alkyl, aryl or heteroaryl group each optionally substituted; and
$R_{25}$ is an optionally substituted $C_1$–$C_6$alkyl, aryl, or heteroaryl group; or
the stereoisomers thereof or the pharmaceutically acceptable salts thereof.

The present invention also provides methods and compositions useful for the therapeutic treatment of central nervous system disorders related to or affected by the 5-HT6 receptor.

The present invention further provides a method for the preparation of compounds of formula I and a compound useful therefor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. At present, there are no known fully selective agonists. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders.

Surprisingly, it has now been found that heterocyclylalkoxy-, -thioxy- or -aminobenzazole derivatives of formula I demonstrate 5-HT6 affinity. Advantageously, said benzazole derivatives may be used as effective therapeutic agents for the treatment of central nervous system (CNS) disorders associated with or affected by the 5-HT6 receptor. Accordingly, the present invention provides heterocyclylalkoxy-, -alkylthio- or -alkylaminobenzazole derivatives of formula I

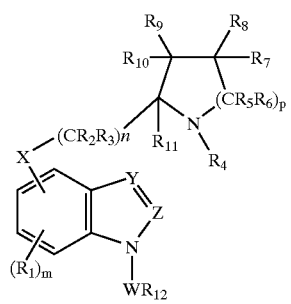

(I)

wherein

W is $SO_2$, CO, CONH, CSNH or $(CH_2)_x$;

X is O, $SO_y$ or $NR_{13}$;

Y is $CR_{14}$ or N;

Z is $CR_{15}$ or N with the proviso that when Y is N then Z must be $CR_{15}$;

m and x are each independently 0 or an integer of 1, 2 or 3;

n and p are each independently an integer of 1, 2 or 3;

$R_1$ is halogen, CN, $OR_{16}$, $CO_2R_{17}$, $CONR_{18}R_{19}$, $CNR_{20}NR_{21}R_{22}$, $SO_2NR_{23}R_{24}$, $SO_wR_{25}$, or a $C_1$–$C_6$alkyl, $C_2$–$C_6$alkenyl, $C_2$–$C_6$alkynyl, $C_3$–$C_6$cycloalkyl, cycloheteroalkyl, phenyl or heteroaryl group each optionally substituted;

$R_2$, $R_3$, $R_5$, $R_6$, $R_7$, $R_8$, $R_9$, $R_{10}$, and $R_{11}$ are each independently H or an optionally substituted $C_1$–$C_6$alkyl group;

$R_4$ is H, $CNR_{26}NR_{27}$, $R_{28}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{12}$ is an optionally substituted $C_1$–$C_6$alkyl, aryl or heteroaryl group;

y and w are each 0 or an integer of 1 or 2;

$R_{13}$ is H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{14}$ and $R_{15}$ are each independently H, halogen or a $C_1$–$C_6$alkyl, aryl, heteroaryl or $C_1$–$C_6$alkoxy group each optionally substituted;

$R_{16}$ is H, $COR_{29}$ or a $C_1$–$C_6$alkyl, $C_2$–$C_6$alkenyl, $C_2$–$C_6$alkynyl, aryl or heteroaryl group each optionally substituted;

$R_{17}$ and $R_{29}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{18}$, $R_{19}$, $R_{20}$, $R_{21}$ $R_{22}$, $R_{26}$, $R_{27}$ and $R_{28}$ are each independently H or an optionally substituted $C_1$–$C_6$alkyl group;

$R_{23}$ and $R_{24}$ are each independently H or a $C_1$–$C_6$alkyl, aryl or heteroaryl group each optionally substituted; and $R_{25}$ is an optionally substituted $C_1$–$C_6$alkyl, aryl, or heteroaryl group; or the stereoisomers thereof or the pharmaceutically acceptable salts thereof.

As used in the specification and claims, the term halogen designates Br, Cl, I or F and the term cycloheteroalkyl designates a $C_5$–$C_7$cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein $X_1$ is NR, O or S.

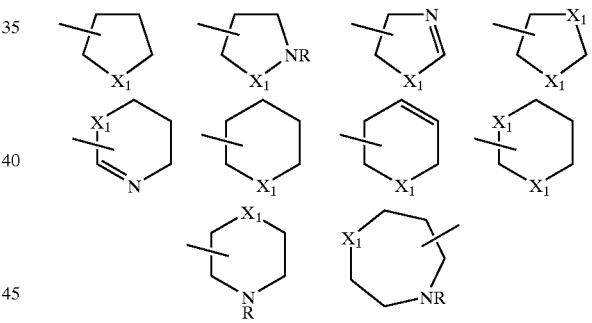

Similarly, as used in the specification and claims, the term heteroaryl designates a 5- to 10-membered aromatic ring system containing 1 or 2 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

In the specification and claims, when the terms $C_1$–$C_6$alkyl, $C_2$–$C_6$alkenyl, $C_2$–$C_6$alkynyl, $C_3$–$C_7$cycloalkyl, cycloheteroalkyl, phenyl or heteroaryl are designated as being optionally substituted, the substituent groups which are optionally present may include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulfonyl, carbamoyl, alkylamido, phenyl, phenoxy, benzyl, benzyloxy, heterocyclyl or cycloalkyl groups, preferably halogen atoms or lower alkyl groups. Typically, 0–3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an opticaly active form.

Preferred compounds of the invention are those compounds of formula I wherein W is $SO_2$ or CO. Also preferred are those compounds of formula I wherein X is O. Another group of preferred compounds of the invention are those compounds of formula I wherein Y is $CR_{14}$. Further preferred compounds of the invention are those compounds of formula I wherein $R_{12}$ is an aryl or heteroaryl group each optionally substituted; and n is 1.

More preferred compounds of the invention are those compounds of formula I wherein W is $SO_2$; X is O; and n is 1. Another group of more preferred compounds of the invention are those compounds of formula I wherein W is $SO_2$; X is O; Y is $CR_{14}$; n is 1; and p is 1.

Among the preferred compounds of the invention are:

1-(phenylsulfonyl)-4-[(2S)-pyrrolidin-2-ylmethoxy]-1H-indole;
1-[(5-chlorothien-2-yl)sulfonyl]-4-[(2S)-pyrrolidin-2-ylmethoxy]-1H-indole;
1-[(2-fluorophenyl)sulfonyl)-4-[(2S)-pyrrolidin-2-ylmethoxy]-1H-indole;
1-[(3-fluorophenyl)sulfonyl)-4-[(2S)-pyrrolidin-2-ylmethoxy]-1H-indole;
1-[(4-fluorophenyl)sulfonyl)-4-[(2S)-pyrrolidin-2-ylmethoxy]-1H-indole;
1-[(3,4-dimethoxyphenyl)sulfonyl)-4-[(2S)-pyrrolidin-2-ylmethoxy]-1H-indole;
4-({4-[2S)-pyrrolidin-2-ylmethoxy]-1H-indole-1-yl}sulfonyl)aniline;
1-(phenylsulfonyl)-4-[(2R)-pyrrolidin-2-ylmethoxy]-1H-indole;
1-(phenylsulfonyl)-4-[(2S)-pyrrolidin-2-ylmethoxy]-1H-indazole;
8-({4-[(2S)-pyrrolidin-2-ylmethoxy]-1H-indazol-1-yl}sulfonyl)quinoline;
1-[(2-chlorophenyl)sulfonyl]-4-[(2S)-pyrrolidin-2-ylmethoxy]-1H-indazole;
1-[(2-fluorophenyl)sulfonyl]-4-[(2S)-pyrrolidin-2-ylmethoxy]-1H-indazole;
1-[(5-chlorothien-2-yl)sulfonyl]-4-[(2S)-pyrrolidin-2-ylmethoxy]-1H-indazole;
4-({4-[(2S)-pyrrolidin-2-ylmethoxy}-1H-indazol-1-yl}sulfonyl)aniline;
2-chloro-4-({4-[(2S)-pyrrolidin-2-ylmethoxy]-1H-indazol-1-yl}sulfonyl)aniline;
1-(phenylsulfonyl)-4-(piperidin-2-ylmethoxy)-1H-indole;
4-{[4-(piperidin-2-ylmethoxy)-1H-indol-1-yl]sulfonyl}aniline;
1-[(2-fluorophenyl)sulfonyl]-4-(piperidin-2-ylmethoxy)-1H-indole;
1-[(5-chlorothien-2-yl)sulfonyl]-4-(piperidin-2-ylmethoxy)-1H-indole;
1-[(3-fluorophenyl)sulfonyl]-4-(piperidin-2-ylmethoxy)-1H-indole;
1-[(2-fluorophenyl)sulfonyl]-4-(piperidin-2-ylmethoxy)-1H-indazole;
1-[(2-chlorophenyl)sulfonyl]-4-(piperidin-2-ylmethoxy)-1H-indazole;
1-[(5-chlorothien-2-yl)sulfonyl]-4-(piperidin-2-ylmethoxy)-1H-indazole;
4-(azepan-2-ylmethoxy)-1-(phenylsulfonyl)-1H-indole;
4-{[4-(azepan-2-ylmethoxy)-1H-indol-1-yl]sulfonyl}aniline;
4-(azepan-2-ylmethoxy)-1-[(2-fluorophenyl)sulfonyl]-1H-indole;
4-(azepan-2-ylmethoxy)-1-[(5-chlorothien-2-yl)sulfonyl]-1H-indole;
4-(azepan-2-ylmethoxy)-1-[(3-fluorophenyl)sulfonyl]-1H-indole;
4-(azepan-2-ylmethoxy)-1-[(2-fluorophenyl)sulfonyl]-1H-indazole;
4-(azepan-2-ylmethoxy)-1-[(2-chlorophenyl)sulfonyl]-1H-indazole;
4-(azepan-2-ylmethoxy)-1-[(5-chlorothien-2-yl)sulfonyl]-1H-indazole;
1-(phenylsulfonyl)-5-(pyrrolidin-2-ylmethoxy)-1H-indole;
1-(phenylsulfonyl)-6-(pyrrolidin-2-ylmethoxy)-1H-indole;
1-(phenylsulfonyl)-5-(pyrrolidin-2-ylmethoxy)-1H-indazole;
1-(phenylsulfonyl)-6-(pyrrolidin-2-ylmethoxy)-1H-indazole; or the stereoisomers thereof or the pharmaceutically acceptable salts thereof.

Compounds of the invention may be prepared using conventional synthetic methods and, if required, standard separation and isolation techniques. For example, compounds of formula I wherein W is $SO_2$; X is O; Y is $CR_{13}$; Z is $CR_{14}$; and $R_4$ and $R_{11}$ are H (Ia) may be prepared by reacting an hydroxyindole of formula II with an N-protected-2-methoxyheterocycle of formula III in the presence of triphenylphosphine and diethyl azodicarboxylate to give the corresponding indol-4-yloxyalkylheterocycle of formula IV. Subsequent sulfonylation and deprotection of the formula IV compound gives the desired formula Ia product. The reaction sequence is illustrated in flow diagram I wherein P represents a protecting group.

Flow Diagram I

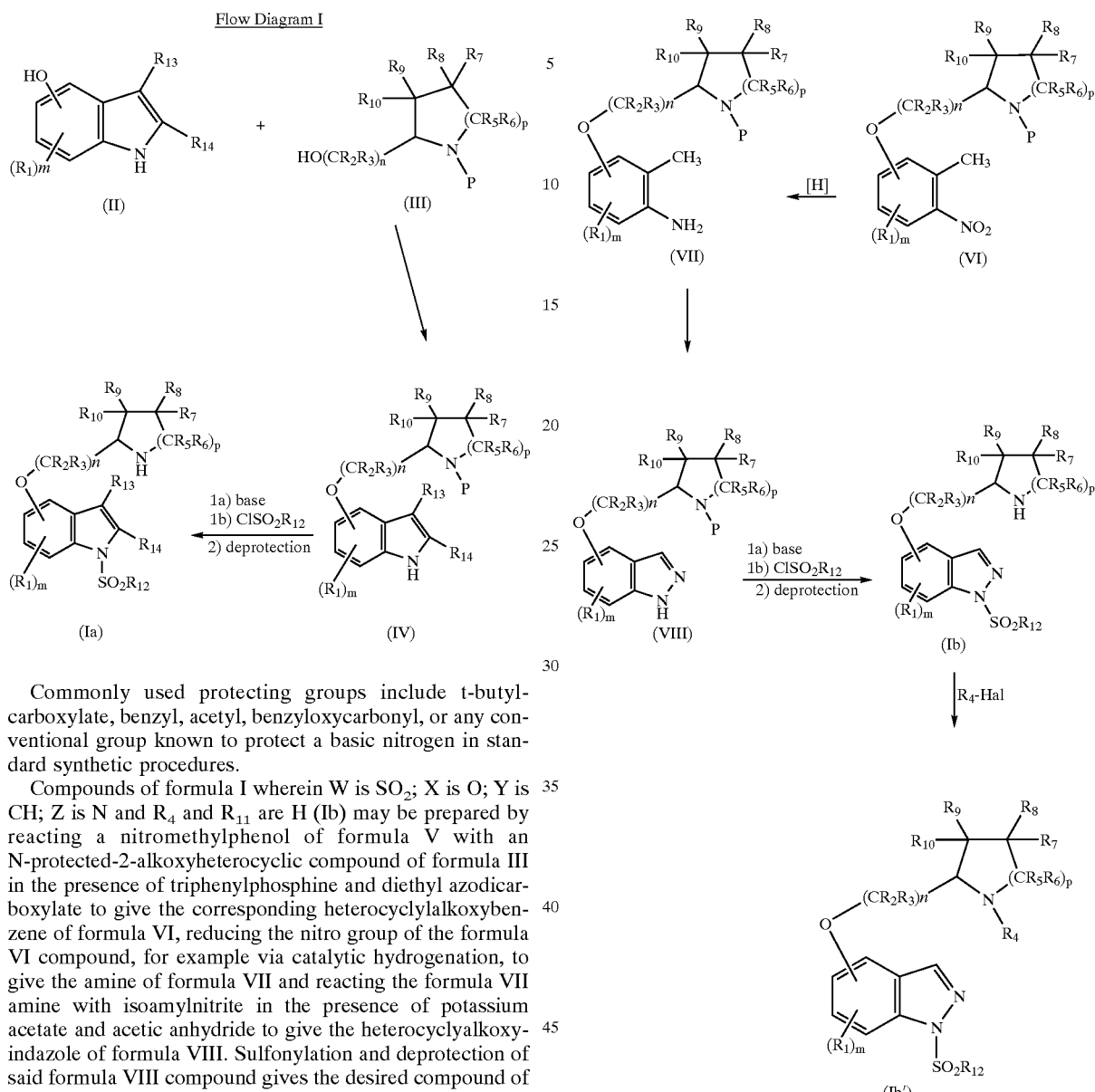

Commonly used protecting groups include t-butyl-carboxylate, benzyl, acetyl, benzyloxycarbonyl, or any conventional group known to protect a basic nitrogen in standard synthetic procedures.

Compounds of formula I wherein W is $SO_2$; X is O; Y is CH; Z is N and $R_4$ and $R_{11}$ are H (Ib) may be prepared by reacting a nitromethylphenol of formula V with an N-protected-2-alkoxyheterocyclic compound of formula III in the presence of triphenylphosphine and diethyl azodicarboxylate to give the corresponding heterocyclylalkoxybenzene of formula VI, reducing the nitro group of the formula VI compound, for example via catalytic hydrogenation, to give the amine of formula VII and reacting the formula VII amine with isoamylnitrite in the presence of potassium acetate and acetic anhydride to give the heterocyclyalkoxyindazole of formula VIII. Sulfonylation and deprotection of said formula VIII compound gives the desired compound of formula Ib wherein $R_4$ is H. Subsequent reaction of the formula Ib compound with a suitable alkylating reagent such as an alkyl or aralkyl halide, $R_4$-Hal, gives those compounds of formula Ib' wherein $R_4$ is other than H. The reaction sequence is shown in flow diagram II wherein P is a protecting group and Hal is Cl, Br or I.

Flow Diagram II

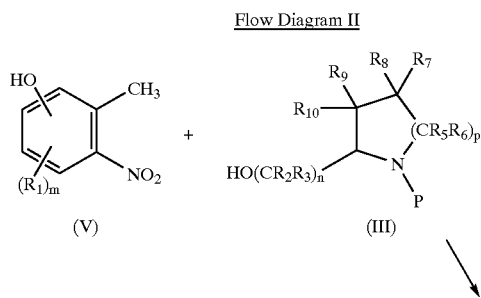

Compounds of formula I wherein W is $SO_2$; X is NH; Y is CH; Z is N; and $R_4$ and $R_{11}$ are H (Ic) may be prepared by the reductive amination of an N-protected carbonylalkylheterocyclic compound of formula X with a nitromethylaniline compound of formula IX to give the compound of formula XI, reducing the nitro group to give the amine of formula XII and reacting the formula XII amine with isoamylnitrite in the presence of potassium acetate and acetic anhydride to give the heterocyclylalkylaminoindazole of formula XIII. Subsequent sulfonylation and deprotection as described hereinabove give the desired compound of formula Ic. The reaction sequence is shown in flow diagram III.

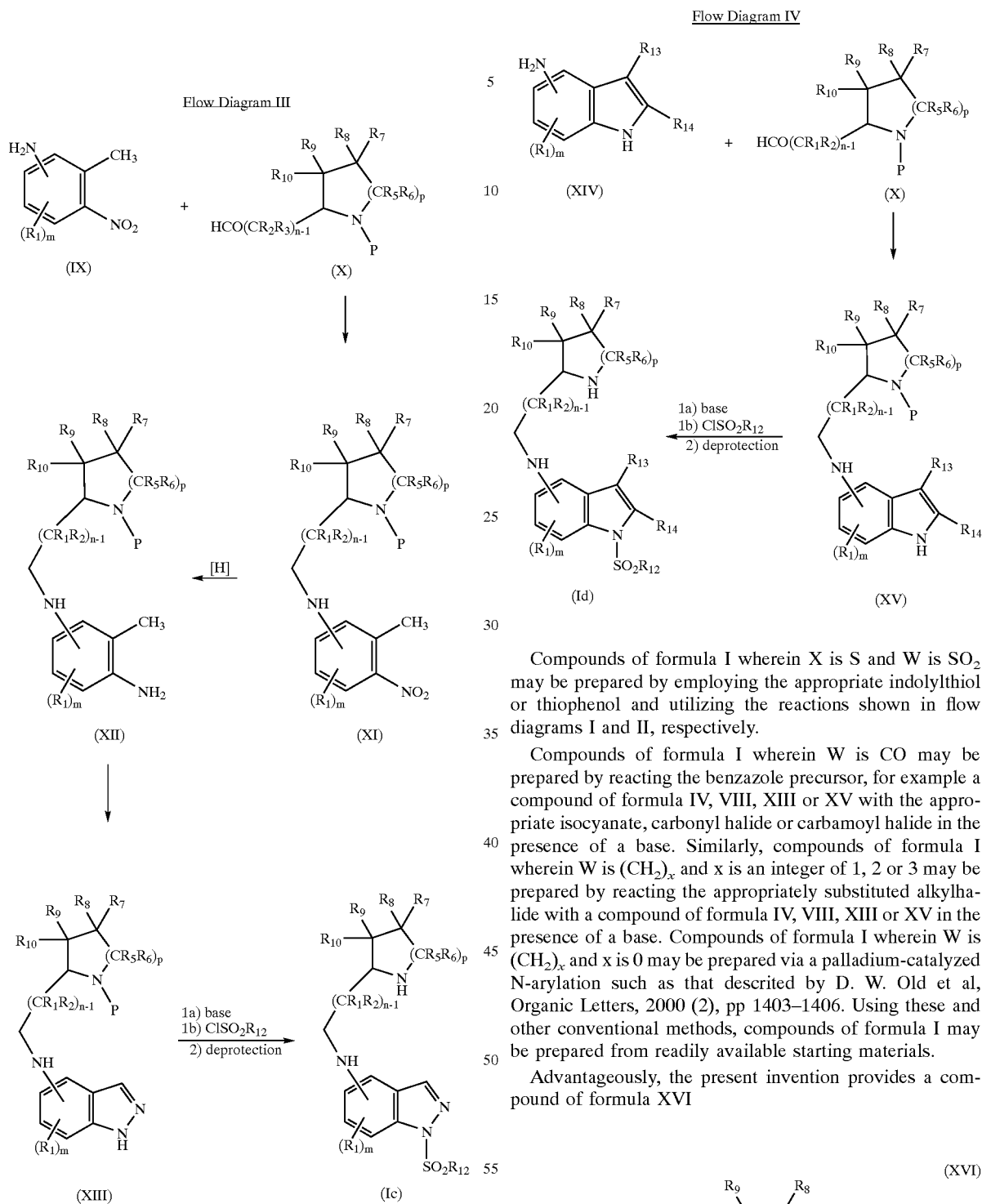

Compounds of formula I wherein X is S and W is $SO_2$ may be prepared by employing the appropriate indolylthiol or thiophenol and utilizing the reactions shown in flow diagrams I and II, respectively.

Compounds of formula I wherein W is CO may be prepared by reacting the benzazole precursor, for example a compound of formula IV, VIII, XIII or XV with the appropriate isocyanate, carbonyl halide or carbamoyl halide in the presence of a base. Similarly, compounds of formula I wherein W is $(CH_2)_x$ and x is an integer of 1, 2 or 3 may be prepared by reacting the appropriately substituted alkylhalide with a compound of formula IV, VIII, XIII or XV in the presence of a base. Compounds of formula I wherein W is $(CH_2)_x$ and x is 0 may be prepared via a palladium-catalyzed N-arylation such as that descrited by D. W. Old et al, Organic Letters, 2000 (2), pp 1403–1406. Using these and other conventional methods, compounds of formula I may be prepared from readily available starting materials.

Advantageously, the present invention provides a compound of formula XVI

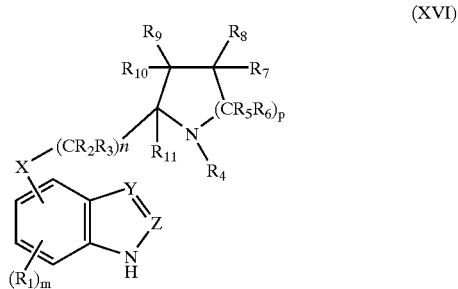

Similarly, compounds of formula I wherein W is $SO_2$; X is NH; Y is $CR_{13}$; Z is $CR_{14}$; and $R_4$ and $R_{11}$ are H (Id) may be prepared by the reductive amination of the formula X carboxyaldehyde with an aminoindole of formula XIV to give the compound of formula XV. Subsequent sulfonylation and deprotection gives the desired product of formula Id. The reaction sequence is shown in flow diagram IV.

wherein X, Y, Z, m, n, p, $R_1$, $R_2$, $R_3$, $R_4$, $R_5$, $R_6$, $R_7$, $R_8$, $R_9$, $R_{10}$ and $R_{11}$ are as defined for formula I. Compounds of formula XVI are useful in the preparation of the therapeutic agents of formula I described hereinabove. Accordingly, the present invention also provides a method for the preparation of a compound of formula I wherein W is $SO_2$ (Ie) which comprises reacting a formula XVI compound with a sulfonyl chloride, $R_{12}SO_2Cl$, wherein $R_{12}$ is as defined for formula I in the presence of a base optionally in the presence of a solvent. The reaction is shown in flow diagram V.

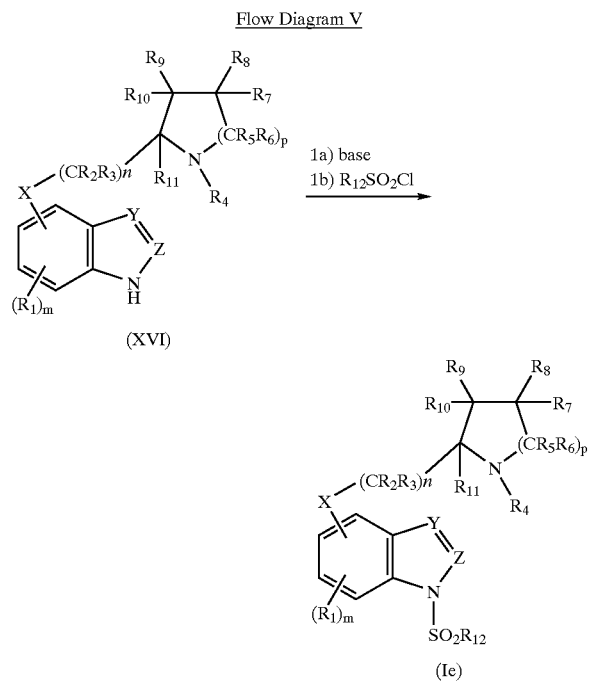

Bases suitable for use in the method of invention are strong bases such as NaH, KOt-Bu, or any conventional base capable of removing a proton from a basic indole or benzazole nitrogen atom.

Advantageously, the inventive compound of formula I may be utilized in the treatment of central nervous system disorders relating to or affected by the 5-HT6 receptor such as motor, mood, psychiatric, cognitive, neurodegenerative, or the like disorders, for example, Alzheimer's disease, Parkinson's disease, attention deficit disorder, anxiety, epilepsy, depression, obsessive compulsive disorder, migraine, sleep disorders, feeding disorders (such as anorexia or bulimia), schizophrenia, memory loss, disorders associated with withdrawl from drug abuse, or the like or certain gastrointestinal disorders such as irritable bowel syndrome. Accordingly, the present invention provides a method for the treatment of a disorder of the central nervous system (CNS) related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The term NMR designates nuclear magnetic resonance. The terms THF and EtOAc designate tetrahydrofuran and ethyl acetate, respectively.

EXAMPLE 1

Preparation of t-Butyl (2S)-2-[(1H-indol-4-yloxy)methyl]-1-pyrrolidinecarboxylate

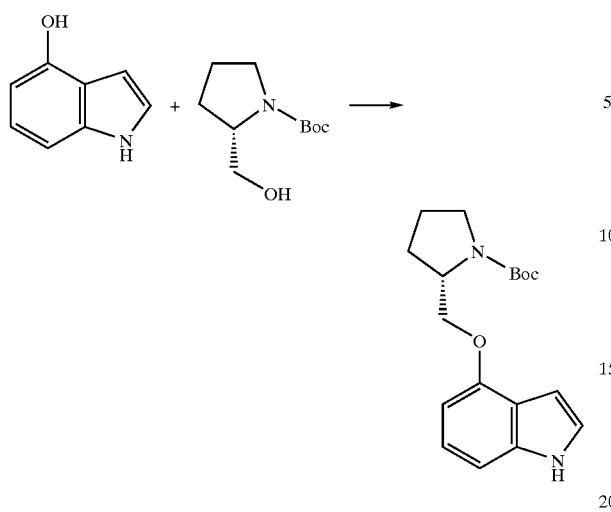

A solution of 4-hydroxyindole (1.33 g, 10.0 mmol), (S)-(−)-1-t-butoxycarbonyl)-2-pyrrolidine methanol (4.02 g, 20.0 mmol) and triphenylphosphine (5.3 g, 20.0 mmol) in THF is treated with diethyl azodicarboxylate (3.2 ML, 20.0 mmol) under nitrogen at room temperature, stirred for 2 h at room temperature and concentrated in vacuo. The resultant residue is purified by flash chromatography (silica gel, EtOAc/hexane: 20/80) to give the title compound as a white solid, 1.5 g, mp 40–41° C., identified by NMR and mass spectral analyses.

EXAMPLE 2
Preparation of t-Butyl (2S)-2-({[1-(phenylsulfonyl)-1H-indol-4-yl]oxy}methyl)-1-pyrrolidinecarboxylate

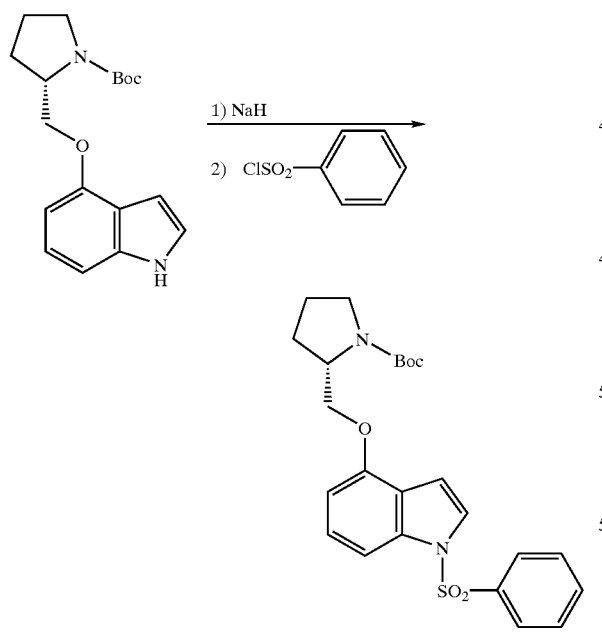

A stirred solution of t-butyl (2S)-2-[(1H-indol-4-yloxy)methyl]-1-pyrrolidinecarboxylate (1.23 g, 3.89 mmol) in THF is treated with sodium hydride (0.17 g, 60% in mineral oil, 4.28 mmol) under nitrogen at room temperature, stirred for 30 minutes, treated with benzenesulfonyl chloride (0.55 mL, 4.28 mmol), stirred at room temperature for 22 h, quenched with ice-water and diluted with EtOAc. The organic phase is separated, washed sequentially with water and brine, dried over MgSO$_4$ and concentrated in vacuo. The resultant residue is purified by flash chromatography (siliga gel, EtOAc/hexanes, 2/8) to afford the title compound as an off-white foam, 1.21 g, mp 48–50° C., identified by NMR and mass spectral analyses.

EXAMPLE 3
Preparation of 1-(Phenylsulfonyl)-4-[(2S)-pyrrolidin-2-ylmethoxy]-1H-indole hydrochloride

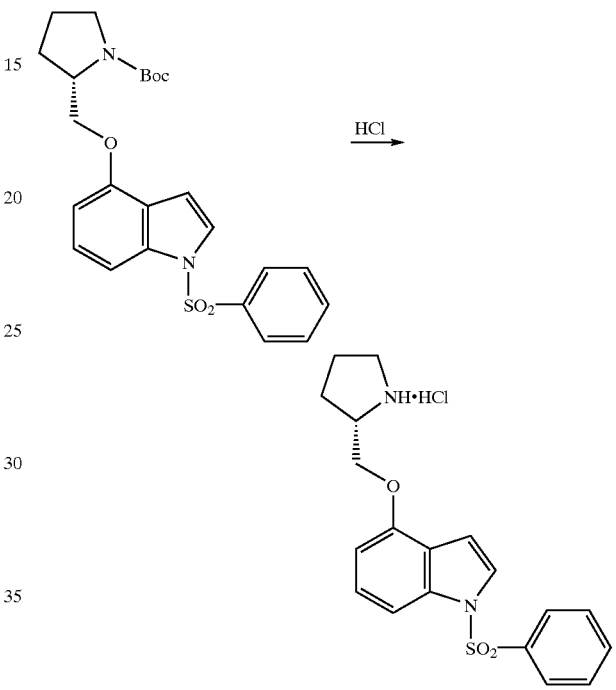

A solution of t-butyl (2S)-2-({[1-phenylsulfonyl)-1H-indol-4-yl]oxy}methyl)-1-pyrrolidinecarboxylate (1.06 g, 2.32 mmol) in methanol and HCl (11.6 mL 1M in ether) is heated at 60° C. under nitrogen for 2 h, cooled to room temperature and concentrated in vacuo. The resultant residue is treated with EtOAc and filtered. The filtercake is dried in vacuo to give the title compound as an off-white solid, 0.89 g, mp 194–196° C., identified by NMR and mass spectral analyses.

EXAMPLES 4–9
Preparation of 1-(Arylsulfonyl)-4-[(2S)-pyrrolidin-2-ylmethoxyl]-1H-indole Hydrochloride

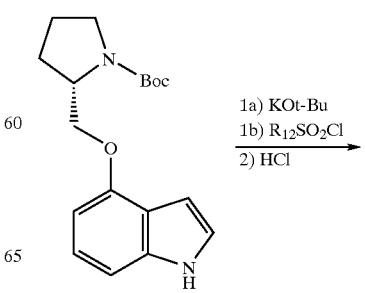

-continued

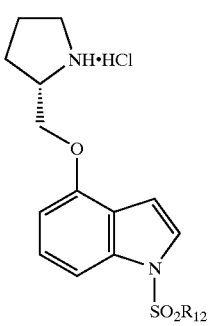

Using essentially the same procedure described in Examples 2 and 3 hereinabove and employing potassium t-butoxide and the appropriate arylsulfonyl chloride, the compounds shown in Table I are obtained and identified by NMR and mass spectral analyses.

TABLE I

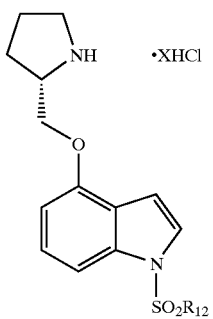

| Example No. | $R_{12}$ | X | mp ° C. |
|---|---|---|---|
| 4 | 5-chlorothien-2-yl | 1 | 204–206 |
| 5 | 2-fluorophenyl | 1 | 153–155 |
| 6 | 3-fluorophenyl | 1 | 160–162 |
| 7 | 4-fluorophenyl | 1 | 258 (dec) |
| 8 | 3,4-dimethoxyphenyl | 1 | 115 (dec) |
| 9 | 4-aminophenyl | 2 | 150 (dec) |

EXAMPLE 10

Preparation of t-Butyl (2R)-2-[(1H-indol-4-yloxy)methyl]pyrrolidine-1-carboxylate

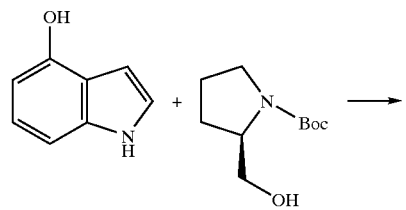

-continued

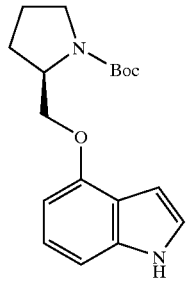

A stirred solution of 4-hydroxyindole (1.33 g, 10.0 mmol), (R)-(+)-1-(t-butoxycarbonyl)-2-pyrrolidinemethanol (4.02 g, 20.0 mmol) and triphenylphosphine (5.3 g, 20.0 mmol) in THF is treated with diethyl azodicarboxylate (3.2 mL, 20 mmol), stirred for 3 h at room temperature and concentrated in vacuo. The resultant residue is treated with EtOAc and filtered through a pad of silica gel. The filtrate is concentrated to give a residue which is purified by chromatography (silica gel, EtOAc:hexanes, 15:80) to afford the title compound as a white solid, 1.08 g, mp 146–147° C.; identified by NMR and mass spectral analyses.

EXAMPLE 11

Preparation of 1-(Phenylsulfonyl)-4-[(2R)-pyrrolidin-2-ylmethoxy]-1H-indole hydrochloride

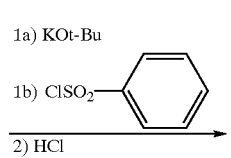

1a) KOt-Bu
1b) ClSO₂—Ph
2) HCl

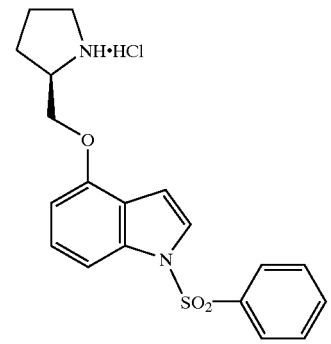

A solution of t-butyl (2R)-2-[(1H-indol-4-yloxy)methyl]pyrrolidine-1-carboxylate (0.316 g, 1.0 mmol) in THF is treated with potassium t-butoxide (1.5 mL, 1.5 mmol, 1M in THF) at room temperature, stirred for 3 min, treated with benzenesulfonyl chloride (0.264 g, 1.5 mmol), stirred for 6 h under nitrogen at room temperature, quenched with 1N aqueous HCl and water and diluted with EtOAc. The organic phase is separated, washed sequentially with water and brine, dried over MgSO₄ and concentrated in vacuo. The resultant residue is treated with HCl (1.5 mL, 1N in Et₂O), heated at reflux temperature for 3 h, cooled to room temperature and filtered. The filtercake is air-dried to afford the title compound as an off-white solid, 0.24 g, mp 204–206° C., identified by NMR and mass spectral analyses.

EXAMPLE 12

Preparation of t-Butyl (2S)-2-[(2-methyl-3-nitrophenoxy)methyl]pyrrolidine-1-carboxylate

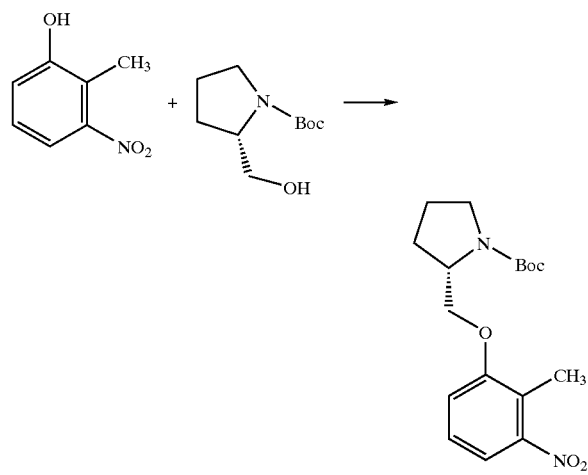

A stirred solution of 2-methyl-3-nitrophenol (3.80 g, 24.84 mmol), (S)-(−)-1-tert-butoxycarbonyl)-2-pyrrolidinemethanol (5.0 g, 24.8 mmol) and triphenylphosphine (6.5 g, 24.8 mmol) in THF is treated with diethylazodicarboxylate (4.3 g, 24.8 mmol), stirred for 3 h at room temperature and concentrated in vacuo. The resultant residue is mixed with ether, stored at 0° C. overnight and filtered. The filtrate is concentrated in vacuo to give a residue which is purified by chromatography (silica gel, EtOAc:hexanes, 20:80) to afford the title compound as a light yellow semisolid, 7.73 g, (91% yield), identified by NMR and mass spectral analyses.

EXAMPLE 13

Preparation of t-Butyl (2S)-2-[(3-amino-2-methylphenoxy)methyl]pyrrolidine-1-carboxylate

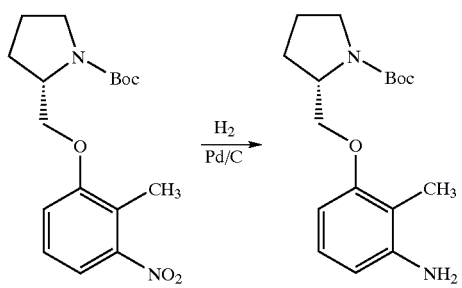

A solution of t-butyl (2S)-2-[(2-methyl-3-nitrophenoxy)methyl]pyrrolidine-1-carboxylate (7.63 g, 21.9 mmol) and 10% Pd/C (0.38 g) in ethanol is hydrogenated (50 psi) at room temperature for 4 h and filtered. The filtrate is concentrated in vacuo to afford the title compound as an off-white solid, 6.66 g, mp 110° C., identified by NMR and mass spectral analyses.

EXAMPLE 14

Preparation of t-Butyl (2S)-2-[(1H-indazol-4-yloxy)methyl]pyrrolidine-1-carboxylate

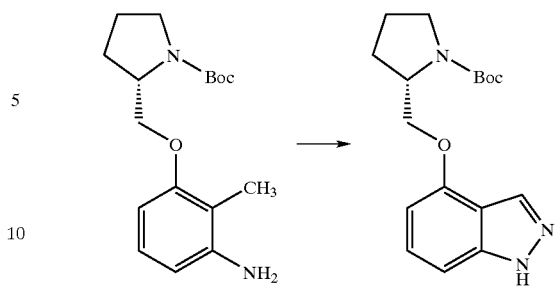

A solution of t-butyl (2S)-2-[(3-amino-2-methylphenoxy)methyl]pyrrolidine-1-carboxylate (5.00 g, 16.33 mmol), potassium acetate (1.92 g, 19.6 mmol) and acetic anhydride (4.9 mL, 52.3 mmol) in benzene is treated dropwise with isoamylnitrite (4.3 mL, 32.7 mmol), heated at reflux temperature overnight, cooled to room temperature and filtered. The filtercake is washed with benzene. The filtrates are combined and concentrated in vacuo to give a yellow oil residue. The residue is purified by chromatography (silica gel, EtOAc:hexanes, 15:85). The purified oil (5.05 g) is dissolved in ethanol, treated with 40% aqueous NaOH, heated at reflux temperature for 45 min, cooled in an ice-water bath, neutralized to pH 8 with concentrated HCl and concentrated in vacuo to remove the ethanol. The resultant aqueous residue is extracted with EtOAc. The combined extracts are washed sequentially with water and brine, dried over $MgSO_4$ and concentrated in vacuo to give a yellow oil. This oil is purified by chromatography (silica gel, EtOAc:hexanes, 30:70) to give the title product as an off-white solid, 3.52 g, mp 125° C., identified by NMR and mass spectral analyses.

EXAMPLE 15

Preparation of 1-(Phenylsulfonyl)-4-[(2S)-pyrrolidin-2-ylmethoxy]-1H-indazole trifluoroacetic acid salt

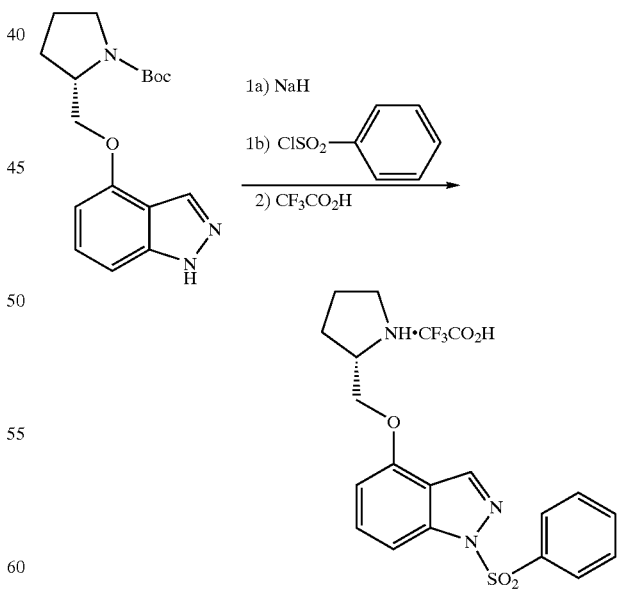

A solution of t-butyl (2S)-2-[(1H-indazol-4-yloxy)methyl]pyrrolidine-1-carboxylate (0.317 g, 1.0 mmol) in dimethylformamide is treated with sodium hydride (0.08 g, 2.0 mmol, 60% in mineral oil) at room temperature, stirred for 10 min, treated with benzenesulfonyl chloride (0.264 g, 1.5 mmol), stirred for 18 h under nitrogen at room temperature, quenched with water and diluted with ether. The organic phase is separated, washed sequentially with water and brine, dried over $MgSO_4$ and concentrated in vacuo to give a white foam residue. The residue is purified by chromatography (silica gel, EtOAc:hexanes, 15:85) to give a white solid. This solid is dissolved in trifluoroacetic acid at 0° C., stirred at room temperature for 90 min and concentrated in vacuo. The resultant residue is triturated under ether to afford the title compound as a white solid, 300 mg, mp 218–219° C., identified by NMR and mass spectral analyses.

EXAMPLES 16–21

Preparation of 1-Arylsulfonyl-4[(2S)-Pyrrolidinylmethoxy] 1H-indazole Hydrochloride

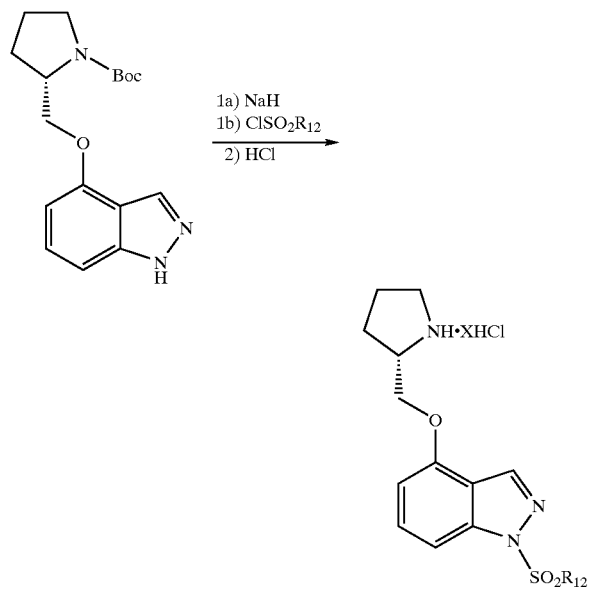

Using essentially the same procedure described in Example 15 hereinabove and employing the appropriate arysulfonyl chloride and anhydrous HCl, the compounds in Table II are obtained and identified by NMR and mass spectral analyses.

TABLE II

| Example No. | $R_{12}$ | X | mp ° C. |
|---|---|---|---|
| 16 | 8-quinolinyl | 0 | 217–218 |
| 17 | 2-chlorophenyl | 1 | >255 (dec) |
| 18 | 2-fluorophenyl | 1 | 145–148 |

TABLE II-continued

| Example No. | $R_{12}$ | X | mp ° C. |
|---|---|---|---|
| 19 | 5-chlorothien-2-yl | 1 | 195 |
| 20 | 4-aminophenyl | 2 | 150–155 |
| 21 | 4-amino-3-chlorophenyl | 2 | 220 (dec) |

EXAMPLE 22

Comparative Evaluation of 5-HT6 Binding Affinity of Test Compounds

The affinity of test compounds for the serotonin 5HT6 receptor is evaluated in the following manner. Cultured Hela cells expressing human cloned 5-HT6 receptors are harvested and centrifuged at low speed (1,000× g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10–25 µl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 µl. To each well is added the following mixture: 80.0 µl of incubation buffer made in 50 mM Tris.HCl buffer (pH 7.4) containing 10.0 mM $MgCl_2$ and 0.5 mM EDTA and 20 µl of [$^3$H]-LSD (S.A., 86.0 Ci/mmol, available from Amersham Life Science), 3.0 nM. The dissociation constant, $K_D$, of the [$^3$H]LSD at the human serotonin 5-HT6receptor is 2.9 nM, as determined by saturation binding with increasing concentrations of [$^3$H] LSD. The reaction is initiated by the final addition of 100.0 µl of tissue suspension. Nonspecific binding is measured in the presence of 10.0 µM methiothepin. The test compounds are added in 20.0 µl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 μl Microscint®-20 scintillant to each shallow well. The unifilter plate is heat-sealed and counted in a PackardTop-Count® with a tritium efficiency of 31.0%.

Specific binding to the 5-HT6 receptor is defined as the total radioactivity bound less the amount bound in the presence of 10.0 μM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the $IC_{50}$ and the $K_i$ values of test compounds with 95% confidence limits. A linear regression line of data points is plotted, from which the $IC_{50}$ value is determined and the $K_i$ value is determined based upon the following equation:

$$K_i = IC_{50}/(1 + L/K_D)$$

where L is the concentration of the radioactive ligand used and $K_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table III, below.

TABLE III

| Test Compound (Ex. No.) | 5-HT6 Binding Ki (nM) |
| --- | --- |
| 3 | 6.0 |
| 4 | 7.0 |
| 5 | 2.0 |
| 6 | 8.0 |
| 7 | 31.0 |
| 8 | 95.0 |
| 9 | 1.0 |
| 11 | 106 |
| 15 | 7.0 |
| 16 | 85.0 |
| 17 | 5.0 |
| 18 | 8.0 |
| 19 | 5.0 |
| 20 | 9.0 |
| 21 | 16.0 |

| Comparative Examples | 5-HT6 Binding Ki (nM) |
| --- | --- |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the results set forth above, the compounds of the present invention have a high degree of affinity for the 5-HT6 receptor.

What is claimed is:

1. A compound of formula I

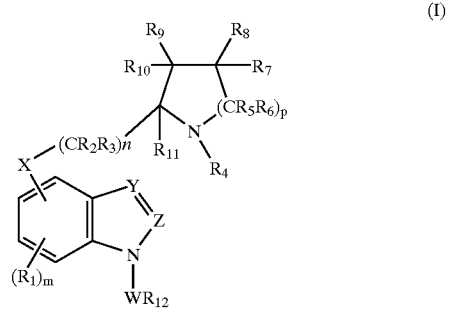

wherein
W is $SO_2$, CO, CONH, CSNH or $(CH_2)_x$;
X is O, $SO_y$ or $NR_{13}$;
Y is $CR_{14}$;
Z is $CR_{15}$;
m and x are each independently 0 or an integer of 1,2 or 3;
n is an integer of 1, 2 or 3;
p is an integer of 1;
$R_1$ is halogen, CN, $OR_{16}$, $CO_2R_{17}$, $CONR_{18}R_{19}$, $CNR_{20}NR_{21}R_{22}$, $SO_2NR_{23}R_{24}$, $SO_wR_{25}$, or a $C_1$–$C_6$alkyl, $C_2$–$C_8$alkenyl, $C_2$–$C_6$alkynyl, $C_3$–$C_6$cycloalkyl, cycloheteroalkyl, phenyl or heteroaryl group each optionally substituted;
$R_2$, $R_3$, $R_5$, $R_6$, $R_7$, $R_8$, $R_9$, $R_{10}$ and $R_{11}$ are each independently H or an optionally substituted $C_1$–$C_6$alkyl group;
$R_4$ is H, $CNR_{26}NR_{27}R_{28}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_{12}$ is an optionally substituted $C_1$–$C_6$alkyl, aryl or heteroaryl group;
y and w are each 0 or an integer of 1 or 2;
$R_{13}$ is H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_{14}$ and $R_{15}$ are each independently H, halogen or a $C_1$–$C_6$alkyl, aryl, heteroaryl or $C_1$–$C_6$alkoxy group each optionally substituted;
$R_{16}$ is H, $COR_{29}$ or a $C_1$–$C_8$alkyl, $C_2$–$C_6$alkenyl, $C_2$–$C_6$alkynyl, aryl or heteroaryl group each optionally substituted;
$R_{17}$ and $R_{29}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_{18}$, $R_{19}$, $R_{20}$, $R_{21}$, $R_{22}$, $R_{26}$, $R_{27}$ and $R_{28}$ are each independently H or an optionally substituted $C_1$–$C_6$alkyl group;
$R_{23}$ and $R_{24}$ are each independently H or a $C_1$–$C_6$alkyl, aryl or heteroaryl group each optionally substituted; and
$R_{25}$ is an optionally substituted $C_1$–$C_6$alkyl, aryl, or heteroaryl group; or
the stereoisomers thereof or the pharmaceutically acceptable salts thereof.

2. The compound according to claim 1 wherein W is $SO_2$.

3. The compound according to claim 1 wherein X is O.

4. The compound according to claim 1 wherein n is 1.

5. The compound according to claim 2 wherein $R_{12}$ is an aryl or heteroaryl group each optionally substituted.

6. The compound according to claim 5 wherein X is O and n is 1.

7. The compound according to claim 6 selected from the group consisting of 1-(phenylsulfonyl)-4-[(2S)-pyrrolidin-2-ylmethoxy]-1H-indole;

1-[(5-chlorothien-2-yl)sulfonyl]-4-[(2S)-pyrrolidin-2-ylmethoxy]-1H-indole;

1-[(2-fluorophenyl)sulfonyl)-4-[(2S)-pyrrolidin-2-ylmethoxy]-1H-indole;

1-[(3-fluorophenyl)sulfonyl)-4-[(2S)-pyrrolidin-2-ylmethoxy]-1H-indole;

1-[(4-fluorophenyl)sulfonyl)-4-[(2S)-pyrrolidin-2-ylmethoxy]-1H-indole;

1-[(3,4-dimethoxyphenyl)sulfonyl)-4-[(2S)-pyrrolidin-2-ylmethoxy]-1H-indole;

4-[(4-[2S)-pyrrolidin-2-ylmethoxy]-1H-indole-1-yl)sulfonyl)aniline;

1-(phenylsulfonyl)-4-[(2R)-pyrrolidin-2-ylmethoxy]-1H-indole;

1-(phenylsulfonyl)-5-(pyrrolidin-2-ylmethoxy)-1H-indole;

1-(phenylsulfonyl)-6-(pyrrolidin-2-ylmethoxy)-1H-indole;

the stereoisomers thereof; and the pharmaceutically acceptable salts thereof.

8. A pharmaceutical composition which comprises a pharmaceutically acceptable carrier and an effective amount of a compound of formula I

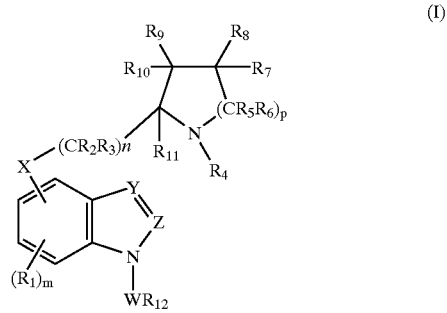

(I)

wherein

W is $SO_2$, CO, CONH, CSNH or $(CH_2)_x$;

X is O, $SO_y$ or $NR_{13}$;

Y is $CR_{14}$;

Z is $CR_{15}$;

m and x are each independently 0 or an integer of 1, 2 or 3;

n is an integer of 1, 2 or 3;

p is an integer of 1;

$R_1$ is halogen, CN, $OR_{16}$, $CO_2R_{17}$, $CONR_{18}R_{19}$, $CNR_{20}NR_{21}R_{22}$, $SO_2NR_{23}R_{24}$, $SO_wR_{25}$, or a $C_1$–$C_6$alkyl, $C_2$–$C_6$alkenyl, $C_2$–$C_6$alkynyl, $C_3$–$C_6$cycloalkyl, cycloheteroalkyl, phenyl or heteroaryl group each optionally substituted;

$R_2$, $R_3$, $R_5$, $R_6$, $R_7$, $R_8$, $R_9$, $R_{10}$ and $R_{11}$ are each independently H or an optionally substituted $C_1$–$C_6$alkyl group;

$R_4$ is H, $CNR_{26}NR_{27}R_{28}$ or a $C_1$–$C_8$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{12}$ is an optionally substituted $C_1$–$C_6$alkyl, aryl or heteroaryl group;

y and w are each 0 or an integer of 1 or 2;

$R_{13}$ is H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{14}$ and $R_{15}$ are each independently H, halogen or a $C_1$–$C_6$alkyl, aryl, heteroaryl or $C_1$–$C_6$alkoxy group each optionally substituted;

$R_{16}$ is H, $COR_{29}$ or a $C_1$–$C_6$alkyl, $C_2$–$C_6$alkenyl, $C_2$–$C_6$alkynyl, aryl or heteroaryl group each optionally substituted;

$R_{17}$ and $R_{29}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{18}$, $R_{19}$, $R_{20}$, $R_{21}$, $R_{22}$, $R_{26}$, $R_{27}$ and $R_{28}$ are each independently H or an optionally substituted $C_1$–$C_6$alkyl group;

$R_{23}$ and $R_{24}$ are each independently H or a $C_1$–$C_6$alkyl, aryl or heteroaryl group each optionally substituted; and $R_{25}$ is an optionally substituted $C_1$–$C_6$alkyl, aryl, or heteroaryl group; or the stereoisomers thereof or the pharmaceutically acceptable salts thereof.

9. The composition according to claim 8 having a formula I compound wherein W is $SO_2$.

10. The composition according to claim 9 having a formula I wherein X is O.

11. The composition according to claim 9 having a formula I compound wherein n is 1.

12. The composition according to claim 11 having a formula I compound selected from the group consisting of:

1-(phenylsulfonyl)-4-[(2S)-pyrrolidin-2-ylmethoxy]-1H-indole;

1-[(5-chlorothien-2-yl)sulfonyl]-4-[(2S)-pyrrolidin-2-ylmethoxy]-1H-indole;

1-[(2-fluorophenyl)sulfonyl)-4-[(2S)-pyrrolidin-2-ylmethoxy]-1H-indole;

1-[(3-fluorophenyl)sulfonyl)-4-[(2S)-pyrrolidin-2-ylmethoxy]-1H-indole;

1-[(4-fluorophenyl)sulfonyl)-4-[(2S)-pyrrolidin-2-ylmethoxy]-1H-indole;

1-[(3,4-dimethoxyphenyl)sulfonyl)-4-[(2S)-pyrrolidin-2-ylmethoxy]-1H-indole;

4-({4-[2S)-pyrrolidin-2-ylmethoxyl-1H-indole-1-yl}sulfonyl)aniline;

1-(phenylsulfonyl)-4-[(2R)-pyrrolidin-2-ylmethoxy]-1H-indole;

1-(phenylsulfonyl)-5-(pyrrolidin-2-ylmethoxy)-1H-indole;

1-(phenylsulfonyl)-6-(pyrrolidin-2-ylmethoxy)-1H-indole;

the stereoisomers thereof; and the pharmaceutically acceptable salts thereof.

\* \* \* \* \*